United States Patent [19]
Adams et al.

[11] 3,957,821

[45] May 18, 1976

[54] XANTHENYL SEMICARBAZIDES

[75] Inventors: Stewart Sanders Adams; Bernard John Armitage; Norman William Bristow; Bernard Vincent Heathcote, all of Nottingham, England

[73] Assignee: The Boots Company Limited, England

[22] Filed: July 29, 1974

[21] Appl. No.: 492,399

Related U.S. Application Data

[60] Division of Ser. No. 277,410, Aug. 2, 1972, Pat. No. 3,842,178, which is a division of Ser. No. 858,183, Sept. 15, 1969, Pat. No. 3,686,218, which is a continuation-in-part of Ser. No. 662,587, Aug. 23, 1967, Pat. No. 3,644,420.

[30] Foreign Application Priority Data

| | | |
|---|---|---|
| Sept. 2, 1966 | United Kingdom | 39384/66 |
| Apr. 5, 1967 | United Kingdom | 15692/67 |
| Sept. 27, 1968 | United Kingdom | 46085/68 |

[52] U.S. Cl. .................................. 260/335; 424/283
[51] Int. Cl.² ........................................ C07D 311/90
[58] Field of Search .................................... 260/335

[56] References Cited

OTHER PUBLICATIONS

M. W. Adriani, Recueil des Travaux Chimiques des Pays–Bas et de la Belgique, Vol. 35, No. 1 (1915) pp. 180–210.

*Primary Examiner*—Norma S. Milestone
*Attorney, Agent, or Firm*—Gordon W. Hueschen

[57] ABSTRACT

4-(9-Xanthenyl)semicarbazide and thiosemicarbazide, 4-(9-thiaxanthenyl)semicarbazide and thiosemicarbazide, and derivatives of these compounds, useful as anti-secretory agents.

5 Claims, No Drawings

XANTHENYL SEMICARBAZIDES

This application is a division of application Ser. No. 277,410, filed 2nd Aug. 1972, now U.S. Pat. No. 3,842,178, issued 15th Oct. 1974, which application in turn is a division of our copending Application Ser. No. 858,183, filed Sept. 15th, 1969, now U.S. Pat. No. 3,686,218, issued 22nd Aug. 1972, which in turn is a continuation-in-part of our application Ser. No. 662,587, filed 23rd Aug. 1967, now U.S. Pat. No. 3,644,420, the entire disclosure of which is incorporated herein by reference. The subject matter of this application was subjected to a requirement for restriction in application Ser. No. 858,183, Paper No. 4.

The invention relates to new derivatives of xanthen and thiaxanthen which have valuable biological activity.

According to one feature of the invention there are provided compounds of formula I

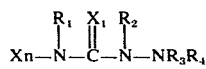

I wherein Xn represents the group

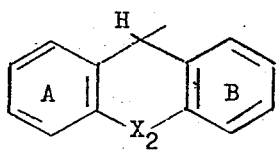

in which $X_1$ and $X_2$ are oxygen or sulphur;

the rings A and B may optionally contain substituents selected from halogen, alkyl, alkoxy and hydroxy;

$R_1$ is hydrogen, alkyl, substituted alkyl, alkenyl, cycloalkyl, hydroxy, alkoxy, acyloxy or trialkylsilyloxy;

$R_2$ is hydrogen, alkyl, substituted alkyl, alkenyl, cycloalkyl, alkanoyl, or alkoxycarbonyl;

$R_3$ is hydrogen, alkyl, substituted alkyl, alkenyl, cycloalkyl, or alkoxy;

$R_4$ is hydrogen, alkyl, substituted alkyl, alkenyl, cycloalkyl, alkanoyl, or alkoxycarbonyl;

or $R_2$ and $R_3$ taken together represent $-(CH_2)_m-$, where $m$ is 3 or 4, and one of the $-CH_2-$ groups may be replaced by $>CO$;

or $R_3$ and $R_4$ together with the nitrogen atom to which they are attached form a saturated 5-7 membered heterocyclic ring, optionally containing an additional hetero group selected from $>NH$, O, S or $>N$-lower alkyl;

together with pharmaceutically acceptable acid addition salts of compounds of formula I;

and, when $R_3$ and $R_4$ each represent alkyl, substituted alkyl, or alkenyl, or together form a ring as hereinbefore defined, pharmaceutically acceptable quaternary salts of compounds of formula I.

The term "substituted alkyl" includes alkyl radicals containing substituents such as hydroxy, halogen, amino, alkanoylamino, alkoxycarbonylamino, alkylamino, alkanoyl(alkyl)amino, alkoxycarbonyl(alkyl)amino, dialkylamino, aryl, aryloxy, alkoxy, acyloxy, and carboxy (in free acid, salt or ester form).

"Alkanoyl" and "alkoxycarbonyl" preferably indicate such groups containing up to 8 carbon atoms.

"Acyl" indicates the acyl residue of a carboxylic acid; such acids include aliphatic carboxylic acids, preferably $C_{1-8}$, aromatic carboxylic acids, heterocyclic carboxylic acids, carbonic acids, N-alkylcarbamic acids, N,N-dialkylcarbamic acids, N-phenylcarbamic acid, N,N-tetramethylene carbamic acid, N,N-pentamethylenecarbamic acid, N,N-3-oxapentamethylenecarbamic acid and N,N-3-thiapentamethylenecarbamic acid.

"Alkyl" whenever used above preferably indicates lower alkyl, containing up to 7 carbon atoms.

Acids which may be used in the quaternary salts defined above may be any conventional quaternisation acids which lead to pharmaceutically acceptable salts, for example HX (where X is halogen) and toluenesulphonic acids.

The methods that can be used to prepare the compounds of formula I depend to some extent upon the nature of $R_{1-4}$; by way of example the following typical methods are shown:

a. by reaction of a xanthydrol or thiaxanthydrol of formula XnOH (or an ester thereof) with a compound of formula II

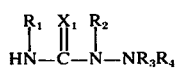

II;

b. by reaction of a compound of formula III $XnNCX_1$  III with a hydrazine of formula IV

  IV c. by reaction of a compound of formula V $XnCON_3$  V with a hydrazine of formula IV;

d. by reaction of a compound of formula VI

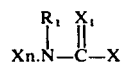  VI wherein X is halogen, with a hydrazine of formula IV. Obvious chemical equivalents (in this type of reaction) of compounds of formula VI may also be used such as compounds of formula VI wherein X is $N_3$, $NCX_1$ or $-X_1$-acyl;

e. by reaction of a compound of formula VII $Xn - Y$  VII with a compound of formula VIII

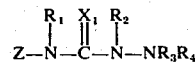  VIII in which one of Y and Z is a halogen atom and the other is one equivalent of a metal, preferably sodium, potassium or lithium;

f. by reaction of an ester of a compound of formula IX

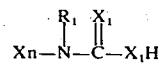  IX with a hydrazine of formula IV; preferred esters include those of formulae X and XI

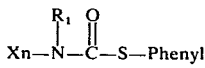  X

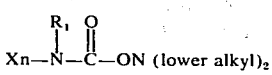  XI;

g. by reaction of a compound of formula XII $$Xn - NHR_1 \quad \quad XII$$

with a carbazoylating or thiocarbazoylating agent capable of providing the

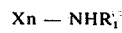

group; examples of such agents, which are chemical equivalents in this type of reaction, are the following:

1. an ester of a compound of formula XIII

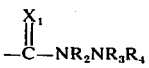  XIII;

a preferred ester is $R_3R_4N-N(R_2)C(O)S$-Phenyl;

2. a compound of formula XIV

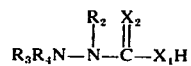  XIV p1 wherein X is halogen or an obvious chemical equivalent (in this type of reaction) such as $N_3$, $NCX_1$ or $-X_1$-acyl;

3. a compound of formula XV

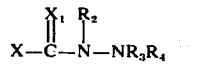  XV and 4. a compound of formula XVI

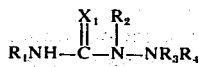  XVI;

h. by reduction of a compound of formula XVII

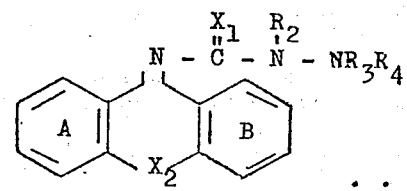  ... XVII, by conventional means, for example by hydrogenation in the presence of standard catalysts such as platinum, palladium, and the like, to give a compound of formula I wherein $R_1$ is hydrogen;

i. by reduction of a compound of formula XVIII

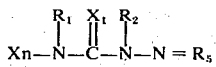  XVIII in which $R_5$ is alkylidene, cycloalkylidene or alpha-alkoxyalkylidene to give a compound of formula I wherein one or both of $R_3$ and $R_4$ are hydrogen; reduction is carried out by conventional means, for example by hydrogenation in the presence of standard catalysts such as platinum, palladium, and the like or by the use of sodium in a lower alkanol;

j. by reductive alkylation of a compound of formula XIX

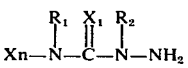  XIX by conventional means, for example using an an aldehyde or ketone of formula $R_6COR_7$ (wherein $R_6$ is alkyl and $R_7$ is hydrogen or alkyl) and hydrogen in the presence of a standard catalyst such as platinum, palladium, and the like, to give compounds of formula I wherein $R_3$ is hydrogen and $R_4$ is alkyl.

k. by alkylation, alkanoylation or alkoxycarbonylation by conventional means of a compound of formula I in which at least one of $R_{1-4}$ is a hydrogen atom to give the corresponding N-alkyl, N-alkanoyl or N-alkoxycarbonyl compound.

l. by N-alkanoylation, N-alkoxycarbonylation or O-acylation by conventional means of a compound of formula I containing an NH or OH group to give the corresponding N-alkanoyl, N-alkoxycarbonyl or O-acyl compound;

m. by dealkanoylation, dealkoxycarbonylation or deacylation of a compound of formula I containing an N-alkanoyl, N-alkoxycarbonyl or O-acyl group respectively to give the corresponding >NH or —OH compound;

n. by alkylation or trialkylsilylation of a compound of formula I containing an OH group to give the corresponding alkoxy or trialkylsilyloxy compound;

o. by hydrogenolysis of a compound of formula XX

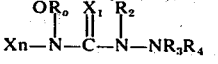  XX wherein $R_o$ is a protecting group readily removable by hydrogenolysis; a preferred protecting group $R_o$ is benzyl, but chemical equivalents (in this type of reaction) of this group will be readily apparent to the skilled chemist; examples include methyl substituted by 2 or 3 phenyl groups, methyl substituted by 1, 2 or 3 p-nitrophenyl, p-methoxyphenyl or 4-pyridyl groups, alkylsulphonyl, arylsulphonyl, arylthio, substituted arylsulphonyl and substituted arylthio; hydrogenation is carried out by conventional means in the presence of standard catalysts such as platinum, palladium, and the like;

p. by reaction of a compound of formula I wherein $R_3$ and $R_4$ each represent alkyl, substituted alkyl, or alkenyl or together form a ring as hereinbefore defined with a conventional quaternising agent such as an alkyl halide, an alkyl p-toluene sulphonate, and the like, to form a pharmaceutically acceptable quaternary salt;

q. by reduction by conventional means of a compound of formula XXI

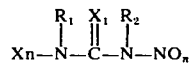
$$Xn-N-C-N-NO_n \qquad \text{XXI}$$
with $R_1$, $X_1$, $R_2$ above.

wherein $n$ is 1 or 2 to give a compound of formula I wherein $R_3$ and $R_4$ are hydrogen; as an example, reduction may be carried out by hydrogenation in the presence of standard catalysts such as platinum, palladium and the like;

r. by reaction of a 3-(9-xanthenyl)rhodanine or a corresponding thiaxanthenyl compound with a hydrazine compound of formula IV;

s. by reaction of a compound of formula XXII

$$Xn-N-CO-NH_2 \qquad \text{XXII}$$
with $R_1$ above.

with a hydrazine of formula IV; and t. by reaction of a compound of formula XVIII with a compound of formula XXIII

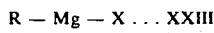
$$R - Mg - X \ldots \text{XXIII}$$

in which R is lower alkyl and X is halogen.

We have found that compounds of formula I are anti-secretory agents, with a specific activity against gastric secretion and without any anticholinergic activity. In particular the compounds reduce or inhibit the secretion of gastric acid in animals; they are therefore useful for reducing or inhibiting gastric secretion (particularly the secretion of gastric acid) and for the treatment of peptic ulceration. (The term "peptic ulceration" is used in its broad sense, as is conventional in the art, to include both gastric ulceration and duodenal ulceration).

The dosage rates of compounds of formula I vary according to the values of $R_{1-4}$, but normally fall within the range ⅓–60 mg. of compound of formula I per kilogram of body weight of subject, preferably administered daily; in the cases of the more active compounds, dosage rates of 0.5–8 mg./kg. are acceptable. The anti-secretory activity of the compounds, which has been demonstrated in the stimulated, pylorus ligated rat, has been found to be better in compounds of formula I wherein $X_1$ and $X_2$ are oxygen than in similar compounds wherein $X_1$ and $X_2$ are sulphur; substitution in rings A and B in general reduces activity.

The compounds of formula I may be administered orally, rectally or parenterally, preferably orally, the optimum dose rate varying with the activity of the compounds. A preferred dosage rate for oral administration is of the order of 25 mg. –4 g. daily, preferably 35 mg. – 600 mg. daily, optionally in divided doses.

According to a further feature of the invention there are provided therapeutic compositions which comprise a compound of formula I in association with pharmaceutical excipients known for the production of compositions suitable for oral, rectal or parenteral administration. The compositions preferably contain 0.1 – 90% by weight of a compound of general formula I.

Compositions for oral administration are the preferred compositions of the invention, and these are the known pharmaceutical forms for such administration, such as for example tablets, capsules, syrups and aqueous and oily suspensions.

The excipients used in the preparation of these compositions are the excipients known in the pharmacist's art.

Preferred compositions are tablets wherein a compound of formula I is mixed with a conventional inert diluent such as lactose in the presence of disintegrating agent, e.g. maize starch and lubricating agents e.g. magnesium stearate. Such tablets may, if desired, be provided with enteric coatings by known methods, for example by the use of cellulose acetate phthalate. Similarly capsules, for example hard or soft gelatin capsules, containing a compound of formula I, with or without other excipients, may be prepared by conventional means and, if desired, provided with enteric coatings in known manner. The tablets and capsules may conveniently each contain 25–500 mg. of a compound of formula I. Other, but less preferred, compositions for oral administration include for example aqueous suspensions containing a compound of formula I in aqueous media in the presence of a non-toxic suspending agent e.g. sodium carboxymethylcellulose and dispersing agents, and oily suspensions containing a compound of formula I in a vegetable oil for example arachis oil.

Compositions of the invention suitable for rectal administration are the known pharmaceutical forms for such administration, such as for example suppositories with cocoa butter or polyethylene glycol bases.

Compositions of the invention suitable for parenteral administration are the known pharmaceutical forms for such administration, for example sterile suspensions in aqueous and oily media or sterile solutions in propylene glycol.

In the compositions of the invention the compounds of formula I may if desired be associated with other compatible pharmacologically active ingredients. For example antacids and acid adsorbents such as aluminium hydroxide and magnesium trisilicate may be included in compositions for oral administration to give an immediate antacid effect. Other pharmacologically active agents which may be associated with the compounds of formula I include compounds active on the central nervous system, including short and long acting sedatives such as the barbiturates and methaqualone, antihistaminic and/or antiemetic agents such as cyclizine and diphenhydramine, and anticholinergic agents such as atropine.

Milk and milk solids are valuable in the treatment of peptic ulcer, and the compositions of the invention include liquid and solid compositions based on milk and milk solids.

According to another aspect of the invention there is provided a method of reducing gastric secretion, especially the secretion of gastric acid, which method comprises administering to a subject an anti-secretory effective amount of a compound of formula I preferably orally.

According to another aspect of the invention there is provided a method of treating peptic ulcer which comprises administering to a subject an anti-secretory effective amount of a compound of formula I preferably orally.

Typical compounds which exemplify the possible values of $R_{1-4}$ are the following:

1,1-dimethyl-4-(9-xanthenyl)semicarbazide
1,1-pentamethylene-4-(9-xanthenyl)semicarbazide
2-methyl-1,1-pentamethylene-4-(9-xanthenyl)-semicarbazide
1,1-tetramethylene-4-(9-xanthenyl)semicarbazide
1,1-hexamethylene-4-(9-xanthenyl)semicarbazide
1,1-diethyl-4-(9-xanthenyl)semicarbazide
1,1-dimethyl-4-(9-xanthenyl)thiosemicarbazide
4-hydroxy-4-(9-xanthenyl)semicarbazide
4-(1-chloro-9-xanthenyl)-1,1-dimethylsemicarbazide
1,1-dimethyl-4-(1-methyl-9-xanthenyl)semicarbazide
1,1,4-trimethyl-4-(9-xanthenyl)semicarbazide
4-methyl-4-(9-xanthenyl)semicarbazide
4-methoxy-4-(9-xanthenyl)semicarbazide
4-isopropoxy-4-(9-xanthenyl)semicarbazide
4-isopropoxy-1,1-dimethyl-4-(9-xanthenyl)semicarbazide
4-(9-xanthenyl)semicarbazide
2-methyl-4-(9-xanthenyl)semicarbazide
4-(9-thiaxanthenyl)semicarbazide
4-hydroxy-1,1-dimethyl-4-(9-xanthenyl)semicarbazide
4-hydroxy-1,1-dimethyl-4-(9-thiaxanthenyl)semicarbazide
1-acetyl-4-(9-xanthenyl)semicarbazide
4-acetoxy-1,1-dimethyl-4-(9-xanthenyl)semicarbazide
1,1-dimethyl-4-propionyloxy-4-(9-xanthenyl)-semicarbazide
4-isobutyryloxy-1,1-dimethyl-4-(9-xanthenyl)-semicarbazide
4-butyryloxy-1,1-dimethyl-4-(9-xanthenyl)semicarbazide
4-hexanoyloxy-1,1-dimethyl-4-(9-xanthenyl)-semicarbazide
1-ethoxycarbonyl-4-(9-xanthenyl)semicarbazide
1,2-dimethyl-4-(9-xanthenyl)semicarbazide
1-isopropyl-4-(9-xanthenyl)semicarbazide
1,1,2-trimethyl-4-(9-xanthenyl)semicarbazide
N-trimethylammonio-N'-9-xanthenylurea iodide
1,1-diethyl-4-hydroxy-4(9-xanthenyl)semicarbazide
4-hydroxy-1,1-dipropyl-4-(9-xanthenyl)semicarbazide
4-hydroxy-1,1-pentamethylene-4-(9xanthenyl)-semicarbazide
4-hydroxy-1,1,2-trimethyl-4-(9-xanthenyl)semicarbazide
4-hydroxy-1,1-tetramethylene-4-(9-xanthenyl)-semicarbazide
4-benzyloxy-1,1-dimethyl-4-(9-xanthenyl)semicarbazide
4-hydroxy-2-methyl-4-(9-xanthenyl)semicarbazide
4-hydroxy-1,2-dimethyl-4-(9-xanthenyl)semicarbazide
2-ethyl-4-hydroxy-4-(9-xanthenyl)semicarbazide
1,2-diethyl-4-hydroxy-4-(9-xanthenyl)semicarbazide
4-hydroxy-1,1-dimethyl-2-propyl-4-(9-xanthenyl)-semicarbazide
4-hydroxy-1,2-dipropyl-4-(9-xanthenyl)semicarbazide
1,1-dibutyl-4-hydroxy-4-(9-xanthenyl)semicarbazide
4-hydroxy-1,1-(3-oxapentamethylene)-4-(9-xanthenyl)semicarbazide
1-acetyl-4-hydroxy-4-(9-xanthenyl)semicarbazide
2β-carboxyethyl-4-hydroxy-4-(9-xanthenyl)semicarbazide lactam
4-hydroxy-2-methyl-1,1-pentamethylene-4-(9-xanthenyl)semicarbazide
4-ethyl-4-(9-xanthenyl)semicarbazide
1-ethyl-4-(9-xanthenyl)semicarbazide
1-ethyl-1-methyl-4-(9-xanthenyl)semicarbazide
4-(9-xanthenyl)thiosemicarbazide
4-methyl-4-(9-xanthenyl)thiosemicarbazide
4-hydroxy-4-(9-thiaxanthenyl)semicarbazide
4-acetoxy-1,1-dimethyl-4-(9-thiaxanthenyl)semicarbazide
1-ethyl-4-hydroxy-4-(9-xanthenyl)semicarbazide
4-acetoxy-1-acetyl-1-ethyl-4-(9-xanthenyl)semicarbazide
1,1-dimethyl-4-pivaloyloxy-4-(9-xanthenyl)semicarbazide
4-p-methoxyphenylacetoxy-1,1-dimethyl-4-(9-xanthenyl)semicarbazide
4-methoxyacetoxy-1,1-dimethyl-4-(9-xanthenyl)-semicarbazide
4-ethoxalyloxy-1,1-dimethyl-4-(9-xanthenyl)-semicarbazide
4-furoyloxy-1,1-dimethyl-4-(9-xanthenyl)semicarbazide
4-crotonifoxy-1,1-dimethyl-4-(9-xanthenyl)semicarbazide
4-benzoyloxy-1,1-dimethyl-4-(9-xanthenyl)semicarbazide
4-p-chlorobenzoyloxy-1,1-dimethyl-4-(9-xanthenyl)-semicarbazide
4-ethoxycarbonyloxy-1,1-dimethyl-4-(9-xanthenyl)-semicarbazide
1,1-dimethyl-4-phenylcarbamyloxy-4-(9-xanthenyl)-semicarbazide
4-allyl-1,1-dimethyl-4-(9-xanthenyl)semicarbazide
4-cyclohexyl-1,1-dimethyl-4-(9-xanthenyl)semicarbazide
1,1-dimethyl-4-trimethylsilyloxy-4-(9-xanthenyl)-semicarbazide
2-allyl-4-(9-xanthenyl)semicarbazide
2-allyl-4-methyl-4-(9-xanthenyl)semicarbazide
2-cyclohexyl-4-(9-xanthenyl)semicarbazide
2-cyclohexyl-4-methyl-4-(9-xanthenyl)semicarbazide
2-ethoxycarbonxyl-1,1-dimethyl-4-(9-xanthenyl)-semicarbazide
2-ethoxycarbonyl-1,1,4-trimethyl-4-(9-xanthenyl)-semicarbazide
1,1-diallyl-4-hydroxy-4-(9-xanthenyl)semicarbazide
1-cyclohexyl-1-methyl-4-hydroxy-4-(9-xanthenyl)-semicarbazide
1-ethoxy-1-ethyl-4-hydroxy-4-(9-xanthenyl)semicarbazide
1-ethyl-1-methyl-4-hydroxy-4-(9-xanthenyl)semicarbazide
1,2-tetramethylene-4-(9-xanthenyl)semicarbazide
4-hydroxy-1,2-tetramethylene-4-(9-xanthenyl)-semicarbazide
N'-hydroxy-N-trimethylammonio-N'-9-xanthenylurea iodide
N'-acetoxy-N-trimethylammonio-N'-9-xanthenylurea iodide
4-(1-chloro-9-xanthenyl)-4-hydroxy-1,1-dimethylsemicarbazide
4-(1-fluoro-9-xanthenyl)-4-hydroxy-1,1-dimethylsemicarbazide 4-(2-fluoro-9-xanthenyl)-4-hydroxy-1,1-dimethyl-semicarbazide
4-(1-chloro-9-xanthenyl)semicarbazide
4-(1-fluoro-9-xanthenyl)semicarbazide
4-(2-fluoro-9-xanthenyl)semicarbazide
4-hydroxy-1,1-dimethyl-4-(1-methyl-9-xanthenyl)-semicarbazide
4-hydroxy-4-(1-methoxy-9-xanthenyl)-1,1-dimethyl-semicarbazide
4-hydroxy-4-(1-hydroxy-9-xanthenyl)-1,1-dimethyl-semicarbazide
4-(1-methyl-9-xanthenyl)semicarbazide
4-(1-methoxy-9-xanthenyl)semicarbazide
4-(1-hydroxy-9-xanthenyl)semicarbazide
4-β-methoxycarbonylpropionoxy-1,1-dimethyl-4-(9-xanthenyl)semicarbazide
1,1-dimethyl-4-methylthioacetoxy-4-(9-xanthenyl)-semicarbazide
1,1-dimethyl-4-phenylacetoxy-4-(9-xanthenyl)-semicarbazide
1,1-dimethyl-4-phenoxyacetoxy-4-(9-xanthenyl)-semicarbazide The above illustrates various values of A, B, $X_1$, $X_2$ and $R_{1-4}$ in various combinations but of course it is to be understood that these values are not limited to the combinations named; all possible combinations are within the invention and each value of A, B, $X_1$, $X_2$ and $R_{1-4}$ is to be considered as having been exemplified generically, independent of any particular combination of radicals.

The "acyl" moiety of the typical acyloxy compounds listed may of course be replaced by other acyl groups as hereinbefore defined. Examples of acyl groups are the following:

Alkanoyl, e.g. acetyl, propionyl, butyryl, valeryl, octanoyl, stearyl, pivaloyl, ethoxalyl; substituted alkanoyl, e.g. phenylalkanoyl such as phenylacetyl; substituted phenylalkanoyl containing substituents such as halogen, alkyl, alkoxy, hydroxy, amino, alkylamino, acylamino, dialklamino or nitro in the phenyl ring; phenoxyalkanoyl such as phenoxyacetyl; substituted phenoxyalkanoyl containing substituents such as halogen, alkyl, alkoxy, hydroxy, amino, alkylamino, acylamino, dialkylamino, or nitro in the phenyl ring; haloalkanoyl such as beta-chloropropionyl; alkoxyalkanoyl such as methoxyacetyl; alkylthioalkanoyl such as methylthioacetyl; dialkylaminoalkanoyl such as diethylaminoacetyl; acyl alkanoyl such as acetoacetyl; cycloalkyl alkanoyl such as cyclohexylacetyl; carboxyalkanoyl such as beta-carboxypropionyl, carboxyalkenoyl such as beta-carboxyacryloyl, and similar groups in ester or salt form; heterocyclic alkanoyl such as pyridineacetyl;
alkenoyl e.g. crotonyl;
cycloalkanoyl e.g. cyclohexylcarbonyl;
aroyl e.g. benzoyl, naphthoyl, susbstituted benzoyl in which the phenyl ring contains substituents such as halogen, alkyl, alkoxy, hydroxy, amino, alkylamino, acylamino, dialkylamino, nitro or carboxyl (and esters and salts thereof);
residues of carbonic acid e.g. alkoxycarbonyl such as methoxycarbonyl, ethoxycarbonyl; substituted alkoxycarbonyl such as 2-methoxyethoxycarbonyl, 2-phenoxyethoxycarbonyl, 2-chloroethoxycarbonyl, 2,2,2-trichloroethoxycarbonyl; alkenyloxycarbonyl such as allyloxycarbonyl; cycloalkoxycarbonyl such as cyclohexyloxycarbonyl; aryloxycarbonyl such as phenoxycarbonyl and similar groups containing halogen, alkyl, alkoxy, hydroxy, amino, alkylamino, acylamino, dialkylamino or nitro substituents in the phenyl ring; aralkoxycarbonyl such as 2-phenylethoxycarbonyl;
N-substituted carbamoyl e.g. N-alkylcarbamoyl such as N-methylcarbamoyl; N,N-dialkylcarbamoyl such as N,N-dimethylcarbamoyl; N-phenylcarbamoyl; N,N-tetramethylenecarbamoyl; N,N-pentamethylenecarbamoyl;
N,N-3-oxapentamethylenecarbamoyl; N,N-3-thiapentamethylenecarbamoyl;
heterocyclic carbonyl e.g. groups comprising a carbon radical attached to a 5 – 7 membered heterocycl ring containing up to two hetero atoms selected from oxygen, sulphur and nitrogen, such as thio tetrahydrothiophen, furan, tetrahydrofuran, pyridine, benzothiazole, benzofuran, xanthen, pyrimidine.

The following non-limitative examples illustrate the invention.

EXAMPLE 1

A solution of xanthydrol (4 g.) and 1,1-dimethy semicarbazide (2 g.) in ethanolic acetic acid (1:1 50 ml.) was left overnight at room temperature. A dilution with ice/water, the solid obtained was recrystallised from chloroform/petroleum ether b.p. 60°C. to give 1,1-dimethyl-4-(9-xanthenyl)semicarbazide m.p. 187°–188°C.

In a similar manner using the appropriate semicarbazide or thiosemicarbazide in place of 1,1-dimsemicarbazide, there were prepared:

1,1-pentamethylene-4-(9-xanthenyl)semicarbazide, m.p. 202°–202.5°C. (from chloroform/petroleum ether b.p. 40°–60°C.)
2-methyl-1,1-pentamethylene-4-(9-xanthenyl)-semicarbazide, m.p. 153°–155°C. (from petroleum ether b.p. 62–68°C., and a trace of chloroform)
1,1-tetramethylene-4-(9-xanthenyl)semicarbazide, m.p. 203°–206°C. (from chloroform/petroleum ether b.p. 40°–60°C.)
1,1-hexamethylene-4-(9-xanthenyl)semicarbazide, m.p. 201–202°C. (from chloroform/petroleum ether b.p. 40°–60°C.)
1,1-diethyl-4-(9-xanthenyl)semicarbazide, m.p. 164°–168°C. (from chloroform/petroleum ether b.p. 40°–60°C.)
1,1-dimethyl-4-(9-xanthenyl)thiosemicarbazide, m.p. 215°–217°C. (from acetone)
4-hydroxy-4-(9-xanthenyl)semicarbazide, m.p. 184°–185°C. (from ethyl acetate)
4-(1-chloro-9-xanthenyl)-1,1-dimethylsemicarbazide, m.p. 217°–219°C. (from acetone)
1,1-dimethyl-4-(1-methyl-9-xanthenyl)semicarbazide, m.p. 222°–223°C. (from acetone)

EXAMPLE 2

A solution of N-methyl-N-9-xanthenylcarbamoyl chloride (1.95 g.) in toluene (20 ml.) was added to an ice-cooled solution of N,N-dimethylhydrazine (0.9 g.) in dry ether (10 ml.). After stirring for 20 minutes at 0°C., the reaction mixture was washed with aqueous sodium bicarbonate and water, dried and evaporated. Recrystallisation of the residue from benzene gave 1,1,4-trimethyl-4-(9-xanthenyl)semicarbazide, m.p. 120°–123°C.

In a similar manner using the appropriate carbamoyl chloride and hydrazine hydrate, the following compounds were prepared:

4-methyl-4-(9-xanthenyl)semicarbazide, m.p. 146°–148°C. (from chloroform/petroleum ether b.p. 62°–68°C.)

4-methoxy-4-(9-xanthenyl)semicarbazide, m.p. 141°–143°C. (from chloroform/ether)

4-isopropoxy-4-(9-xanthenyl)semicarbazide, m.p. 134°C. (from cyclohexane)

4-isopropoxy-1,1-dimethyl-4-(9-xanthenyl)semicarbazide, m.p. 157.5°C.

(from cyclohexane). (Prepared using N,N-dimethylhydrazine instead of hydrazine hydrate)

N-Methyl-N-9-xanthenylcarbamoyl chloride was prepared by adding a mixture of N-methyl-9-xanthenylamine (10 g.), triethylamine (7 ml.) and dry toluene (30 ml.) to a 10% solution of phosgene in toluene (250 ml.) at about −17°C. After overnight standing, the reaction product was evaporated at less than 30°C. under reduced pressure to dryness. The residue was boiled with petroleum ether (b.p. 62°–68°C.), triethylamine hydrochloride filtered off, and the filtrate crystallised to give N-methyl-N-9-xanthenylcarbamoyl chloride, m.p. 94°–95°C.

N-Methoxy-N-9-xanthenylcarbamoyl chloride was prepared by adding a mixture of N-methoxy-N-9-xanthenylamine (7 g.), triethylamine (9 ml.) and toluene (10 ml.) to a 10% solution of phosgene in toluene (93 ml.) at −15°C. to −10°C. The reaction mixture was stirred at −10°C. for 15 minutes and then allowed to attain room temperature over 1 hour. Evaporation in vacuo after filtering from triethylamine hydrochloride gave crude N-methoxy-N-9-xanthenylcarbamoyl chloride in the form of a yellow-brown oil. This was used dissolved in toluene.

N-Isopropoxy-N-9-xanthenylcarbamoyl chloride was prepared in a similar manner in the form of a brown oil, and this was used dissolved in toluene.

EXAMPLE 3 a. A solution of S-phenyl N-hydroxy-N-9-xanthenylthiocarbamate (1.7 g.) in pyridine (12.5 ml.) containing triethylamine (0.4 ml.) was treated with hydrazine hydrate (0.78 ml.) at room temperature and left for 4 hours. After heating on the steam bath for 1 hour and overnight standing at room temperature, the reaction mixture was diluted with water (35 ml.) and filtered. The filtrate was diluted with a large volume of water; the resulting precipitate was crystallised from dimethylformamide/toluene to give 4-hydroxy-4-(9-xanthenyl)-semicarbazide, m.p. 186°C.

In a similar manner using S-phenyl N-9-xanthenylthiocarbamate in place of S-phenyl N-hydroxy-N-9-xanthenylthiocarbamate, there was prepared 4-(9-xanthenyl)semicarbazide, m.p. 212°–214°C. (from dimethylformamide/toluene).

In a similar manner using S-phenyl N-9-xanthenylthiocarbamate and methylhydrazine, there was obtained 2-methyl-4-(9-xanthenyl)semicarbazide, m.p. 183°–186°C. (from benzene).

The starting thiocarbamates were prepared as follows. S-Phenylthiocarbonyl chloride (2.8 ml.) was added to a stirred solution of N-9-xanthenylhydroxylamine (2.13 g.) in pyridine (10 ml.) at 0°C. After overnight standing at 0°C., the reaction mixture was diluted with water (100 ml.). The product was isolated in ether (washing with fresh 5% aqueous sodium carbonate) and crystallised from acetone/petroleum ether b.p. 62°–68°C. to give S-phenyl N-hydroxy-N-9-xanthenylthiocarbamate, m.p. 177°–178°C.

In a similar manner using N-9-xanthenylamine in place of N-9-xanthenylhydroxylamine, there was prepared S-phenyl N-9-xanthenylthiocarbamate, m.p. 185°–187°C. (from acetone).

b. O-Chloroformyl ethyl methyl ketoxime (3.3 g.) was added dropwise to a solution of N-9-xanthenylhydroxylamine (4.26 g.) in dry pyridine (20 ml.) at 0°C., and allowed to stand for 1 hour to give a crude solution of ethyl methyl ketoxime N-hydroxy-N-9-xanthenylcarbamate. 5Ml. of this was treated with hydrazine hydrate (1.6 ml.) and left at room temperature for 4 days. The reaction mixture was then poured into a large volume of water and the product isolated in ethyl acetate (35 ml.); this solvent was evaporated and replaced by toluene (8 ml.) and evaporation continued to a residual volume of about 5 ml. The solid which separated was recrystallised from dimethylformamide/toluene to give 4-hydroxy-4-(9-xanthenyl)semicarbazide m.p. 184°C.

c. Ethyl N-9-xanthenylcarbamate (1 g.) and N,N-dimethylhydrazine (5 ml.) were added to a solution of sodium (0.1 g.) in methanol (10 ml.). The mixture was sealed in a pressure vessel and heated at 100°C. for 18 hours, after which time it was evaporated to dryness. Recrystallisation from benzene and then carbon tetrachloride gave 1,1-dimethyl-4-(9-xanthenyl)semicarbazide, m.p. 189°–191°C. (d) Hydrazine hydrate (0.82 ml.) was added to a solution of S-phenyl N-9-thiaxanthenylthiocarbamate (679 mg.) in pyridine (7 ml.) containing triethylamine (1.4 ml.) at 0°C. After 3 hours at 0°C., the reaction mixture was diluted with ice/water (50 ml.) and the resulting precipitate recrystallised from chloroform/petroleum ether b.p. 62°–68°C. to give 4-(9-thiaxanthenyl)semicarbazide, m.p. 199°–201°C. S-Phenyl N-9-thiaxanthenylthiocarbamate (m.p. 161°–165°C. ex acetone/petroleum ether b.p. 62°–68°C.) was prepared from S-phenylthiocarbamoyl chloride and 9-thiaxanthenylamine in a manner similar to that described in (a) for S-phenyl N-hydroxy-N-9-xanthenylthiocarbamate.

EXAMPLE 4

S-Phenylthiocarbonyl chloride (6 ml.) in dioxan (20 ml.) was added dropwise to a stirred, ice-cooled solution of N,N-dimethylhydrazine (5.04 g.) in dioxan (60 ml.). After stirring at 0°C. for 15 minutes, the mixture (containing S-phenyl N',N'-dimethylthiocarbazate) was filtered into a stirred solution of N-9-xanthenyl hydroxylamine (8.96 g.) in pyridine (136 ml.) containing triethylamine (6.4 ml.) at room temperature. After 24 hours, the reaction mixture was diluted with water, and the resulting precipitate recrystallised from dimethylformamide/toluene to give 4-hydroxy-1,1-dimethyl-4-(9-xanthenyl)semicarbazide, m.p. 198°–200°C.

In a similar manner using N-9-thiaxanthenylhydroxylamine in place of N-9-xanthenylhydroxylamine, there was prepared 4-hydroxy-1,1-dimethyl-4-(9-thiaxanthenyl)semicarbazide, m.p. slow decomposition from 181°C. (from dimethylformamide/toluene).

In a similar manner using O-isopropyl-N-9-xanthenylhydroxylamine (b.p. 138°C./3 m.m., prepared by reacting O-isopropylhydroxylamine hydrochloride with xanthydrol in pyridine/ethanol in the presence of acetic acid) in place of N-9-xanthenylhydroxylamine, there was prepared 4-isopropoxy-1,1-dimethyl-4-(9-xanthenyl)semicarbazide, m.p. 159°C. (from cyclohexane).

EXAMPLE 5

4-(9-Xanthenyl)semicarbazide (0.59 g.) in pyridine (10 ml.) was treated with acetic anhydride (0.6 ml.) and left at room temperature for 24 hours. Dilution with water (200 ml.) and crystallisation of the precipitate obtained from dimethylformamide/toluene gaive 1-acetyl4-)9-xanthenyl)semicarbazide, m.p. 226°–228°C.

EXAMPLE 6

A solution of 4-hydroxy-1,1-dimethyl-4-(9-xanthenyl)semicarbazide (897 mg.) in pyridine (10 ml.) was treated with acetic anhydride (612 mg.) and left at room temperature for 24 hours. Dilution with ice/water (100 ml.) and crystallisation of the resulting precipitate from acetone/petroleum ether b.p. 62°–68°C. gave 4-acetoxy-1,1-dimethyl-4-(9-xanthenyl)semicarbazide, m.p. 120°–121°C.

In a similar manner using propionic anhydride in place of acetic anhydride there was obtained 1,1-dimethyl-4-propionyloxy-4-(9-xanthenyl)semicarbazide, m.p. 123°–124°C. (from acetone/petroleum ether b.p. 40°–60°C.).

In a similar manner using isobutyric anhydride there was obtained 4-isobutyryloxy-1,1-dimethyl-4-(9-xanthenyl)semicarbazide, m.p. 131°–132°C. (from acetone).

In a similar manner using butyric anhydride there was obtained 4-butyryloxy-1,1-dimethyl-4-(9-xanthenyl)-semicarbazide, m.p. 115°–117°C. (from acetone/petroleum ether b.p. 62°–68°C.).

In a similar manner using hexanoic anhydride there was obtained 4-hexanoyloxy-1,1-dimethyl-4-(9-xanthenyl)semicarbazide.

EXAMPLE 7

A solution of 4-acetoxy-1,1-dimethyl-4-(9-xanthenyl)semicarbazide (143 mg.) in methanol (5 ml.) was treated with 1N sodium hydroxide solution (0.63 ml.) and left at room temperature for 2 hours. Acetic acid (0.05 ml.) was then added and the reaction mixture diluted with water (5 ml.). The resulting precipitate was dried to give 4-hydroxy-1,1-dimethyl-4-(9-xanthenyl)semicarbazide, m.p. 196°–198°C.

In a similar manner, crude 4-acetoxy-1-acetyl-4-(9-xanthenyl)semicarbazide (prepared by the method of Example 6 from 4-hydroxy-4-(9-xanthenyl)semicarbazide) was hydrolysed to give 1-acetyl-4-hydroxy-4-(9-xanthenyl)semicarbazide, m.p. 173°–176°C. (from dimethylformamide/toluene).

EXAMPLE 8

Xanthen-9-carbonyl azide (4 g.) in benzene (50 ml.) was warmed to 50°–60°C. until nitrogen evolution ceased. To the filtered solution (containing 9-xanthenyl isocyanate) there was added ethoxycarbonylhydrazine (1.67 g.) in benzene (10 ml.). After 1 hour, the reaction product was filtered and the residue recrystallised from dimethylformamide/toluene to give 1-ethoxycarbonyl-4-(9-xanthenyl)semicarbazide, m.p. 188°–191°C.

In a similar manner, using methylhydrazine and N,N'-dimethylhydrazine in place of ethoxycarbonylhydrazine, there were obtained respectively 2-methyl-4-(9-xanthenyl)semicarbazide, m.p. 188°–190°C. (from methanol) and 1,2-dimethyl-4-(9-xanthenyl)semicarbazide, m.p. 118°–119°C.

Xanthen-9-carbonyl azide used above was prepared as follows. Xanthen-9-carbonyl chloride [6.65 g., m.p. 87°–90°C., prepared by refluxing xanthen-9-carboxylic acid (6.34 g.) with thionyl chloride (25 ml.) for 2 hours and evaporating to dryness] was dissolved in acetone (25 ml.) and stirred in an ice bath. Sodium azide (2.5 g.) in water (10 ml.) was added slowly at 12°–17°C., and then water (10ml.) was added to the mixture at 10°C. The precipitate thus obtained was filtered off, washed with cold 50% aqueous acetone (20 ml.) and dried. It was then recrystallised from ether at −80°C. to give xanthen-9-carbonyl azide, decomposition point 72°C.

EXAMPLE 9

Xanthen-9-carbonyl azide (1 g.) and N,N-dimethylhydrazine (0.4 ml.) in dry benzene (15 ml.) were warmed to 60°C., causing an effervescence which was complete in 30 minutes. After 1 hour at 25°C., the precipitate was collected to give 1,1-dimethyl-4-(9-xanthenyl)semicarbazide, m.p. 189°–195°C.

EXAMPLE 10

Acetone 4-(9-xanthenyl)semicarbazone (274 mg.) in methanol (38 ml.), acetic acid (1 ml.) and water (1 ml.) was treated with hydrogen in the presence of platinum oxide (25 mg.). When reduction was complete, the reaction mixture was filtered, the filtrate evaporated to dryness, and the residue recrystallised from benzene to give 1-isopropyl-4-(9-xanthenyl)semicarbazide, m.p. 161.5°–162.5°C.

EXAMPLE 11

4-Benzyloxy-1,1-dimethyl-4-(9-xanthenyl)semicarbazide (389 mg.) in ethanol (25 ml.) was treated with hydrogen in the presence of 10% palladium charcoal (80 mg.). When hydrogenation was complete, the reaction mixture was filtered, the product washed from the catalyst with dimethylformamide (10 ml.) and the solution evaporated to dryness in vacuo. The residue was recrystallised from dimethylformamide/toluene to give 4-hydroxy-1,1-dimethyl-4-(9-xanthenyl)semicarbazide, m.p. 192°–193°C.

In a similar manner from the appropriate 4-benzyloxy-4-(9-xanthenyl)semicarbazide, there were prepared:

1,1-diethyl-4-hydroxy-4-(9-xanthenyl)semicarbazide, (from dimethylformamide) m.p. 208°C.

4-hydroxy-1,1-dipropyl-4-(9-xanthenyl)semicarbazide 4-hydroxy-1,1-pentamethylene-4-(9-xanthenyl)-semicarbazide, m.p. 192°C.

(from dimethylformamide/toluene/petroleum ether b.p. 60°–80°C. 1:1:1).

4-hydroxy-4-(9-xanthenyl)semicarbazide 4-hydroxy-1,1,2-trimethyl-4-(9-xanthenyl(semicarbazide 4-hydroxy-1,1-tetramethylene-4-(9-xanthenyl)-semicarbazide The starting materials were prepared as follows. A mixture of O-benzyl-N-9-xanthenylhydroxylamine (3.03 g.) and triethylamine (1 ml.) in dry toluene (30 ml.) was added dropwise to a 10% solution of phosgene in toluene (30 ml.) maintained at −20°C. After 15 minutes at this temperature and 1 hour to rise to room temperature, the reaction mixture was filtered and the filtrate evaporated in vacuo to give crude N-benzyloxy-N-9-xanthenylcarbamoyl chloride in the form of a brown oil. A solution of this material (about 1 equivalent) in toluene (30 ml.) was added to 1,1-dimethylhydrazine (0.6 g.), triethylamine (1g.) and toluene (30 ml.) at room temperature. After overnight stirring, the reaction mixture was filtered and the filtrate evaporated to dryness in vacuo. Recrystallisation of the residue from cyclohexane/petroleum ether b.p. 62°–68'C. gave 4-benzyloxy1,1-dimethyl-4-(9-xanthenyl)-semicarbazide, m.p. 117°C.

In a similar manner there were prepared:
4-benzyloxy-1,1-diethyl-4-(9-xanthenyl)semicarbazide, (from cyclohexane) m.p. 126.5°–127.5°C.
4-benzyloxy-1,1-dipropyl-4-(9-xanthenyl)semicarbazide, m.p. 82°C. (from chloroform/petroleum ether b.p. 62°–68°C.)
4-benzyloxy-1,1-pentamethylene-4-(9-xanthenyl)-semicarbazide m.p. 143°–144°C. (from chloroform/petroleum ether b.p. 62°–68°C.)
4-benzyloxy-4-(9-xanthenyl)semicarbazide
4-benzyloxy-1,1,2-trimethyl-4-(9-xanthenyl)-semicarbazide
4-benzyloxy-1,1-tetramethylene-4-(9-xanthenyl)-semicarbazide

EXAMPLE 12

A solution of 1,1-dimethylsemicarbazide (1.03 g.) in dry dioxan (20 ml.) was stirred at room temperature for 3 hours with sodium hydride (0.48 g., 50% oil dispersion). 9-Chloroxanthen (2.16 g.) in dioxan (15 ml.) was added dropwise and, after overnight stirring, the mixture was poured into ice/water (100 ml.) containing saturated aqueous sodium bicarbonate (5 ml.). The resulting precipitate was boiled with benzene (20 ml.), cooled and the separated solid extracted with hot carbon tetrachloride (15 ml.). On cooling there was obtained 1,1-dimethyl-4-(9-xanthenyl)semicarbazide, m.p. 193°–194°C.

EXAMPLE 13

Sodium hydride (0.48 g., 50% oil dispersion) was added to a solution of 1,1-dimethyl-4-(9-xanthenyl)-semicarbazide (2.83 g.) in tetrahydrofuran (40 ml.). After 2 hours under reflux, methyl iodide (1.32 ml.) was added and refluxing continued for 5 hours. Methanol (5 ml.) was then added to the cooled and filtered reaction mixture, and the solution evaporated to 10 ml. Chloroform (25 ml.) was added, the solution filtered and then evaporated. The portion of the residue insoluble in hot petroleum ether b.p. 40°–60°C. (2 × 15 ml.) was recrystallised from chloroform to give 1,1,2-trimethyl-4-(9-xanthenyl)semicarbazide, m.p. 141°–142°C.

EXAMPLE 14

A suspension of N-methyl-N-nitroso-N'-xanthenylurea (520 mg.) and platinum oxide (110 mg.) in methaol (20 ml.) was shaken under hydrogen for 12 hours. After filtration, the reaction mixture was evaporated in vacuo to about 1.5 ml. and diluted with water. The precipitate was collected and the benzene-soluble portion crystallised from benzene and from benzene/petroleum ether b.p. 62°–68°C. to give 2-methyl-4-(9-xanthenyl)semicarbazide, m.p. 173°–176°C.

The starting material was prepared as follows. A suspension of N'-methyl-N-9-xanthenylurea (5.08 g.) in acetic acid (75 ml.) and water (5 ml.) at 5°C. was treated with a solution of sodium nitrite (1.52 g.) in water (5 ml.). After ice cooling, the precipitate was collected and recrystallised from ethanol and from benzene/petroleum ether b.p. 62°–68°C. to give the required product, m.p. 151°C.

EXAMPLE 15

A mixture of 1,1-dimethyl-4-(9-xanthenyl)semicarbazide (259 mg.), methyl iodide (0.1 ml.) and acetone (10 ml.) was refluxed for 7 hours. After cooling, the precipitate was recrystallised from nitromethane to give N-trimethylammonio-N'-9-xanthenylurea iodide, m.p. 196°C.

EXAMPLE 15A

A solution of 1,1-dimethyl-4-(9-xanthenylidene)-semicarbazide (100 mg.) in dimethylformamide (7 ml.) was treated with 10% palladium/charcoal and shaken in an atmosphere of hydrogen. After 1 hour, platinum oxide (20 mg.) was added and shaking continued a further hour. The mixture was filtered and the filtrate evaporated to dryness in vacuo. The residue was extracted with boiling carbon tetrachloride, filtered, and the filtrate evaporated to a small bulk; cooling gave 1,1-dimethyl4-(9-xanthenyl)semicarbazide, m.p. 190°–193°C.

The starting material was prepared as follows. S-Phenylthiocarbonylchloride (6 ml.) in dioxan (20 ml.) was added dropwise to a stirred, ice-cooled solution of N,N-dimethylhydrazine (5.06 g.) in dioxan (60 ml.). After stirring at 0°C. for 15 minutes, the mixture (containing S-phenyl N',N'-dimethylthiocarbazate) was filtered into a stirred solution of xanthone imine (4.1 g.) in pyridine (70 ml.) and triethylamine (3 ml.) at room temperature. After 11 days, the mixture was diluted with ice-water (150 ml.) and filtered. After further dilution (500 ml.) the mixture was extracted with ether. Evaporation of the ether solution gave a yellow gummy solid. Trituration of this with a little ether gave 1,1-dimethyl-4-(9-xanthenylidene)semicarbazide, m.p. 168°–169°C. (from acetone/petroleum ether, b.p. 40°–60°C.).

[Satisfactory elemental analyses were obtained for the compounds prepared in the above Examples. Structures were confirmed by infra red spectroscopy and, where necessary, by nuclear magnetic resonance spectroscopy. In many cases, the compounds melted with decomposition at the temperatures described.]

EXAMPLE 16

In the preparation of tablets, mixtures of the following type may be tabletted in conventional manner:

| | |
|---|---|
| Compound of formula I | 10 – 90% |
| Lactose | 0 – 80% |
| Maize starch | 5 – 10% |
| Magnesium stearate | ca. 1% |
| Microcrystalline cellulose | 0 – 90% |
| | (by weight) |

EXAMPLE 17

In the preparation of tablets the following mixture was dry granulated and compressed in a tabletting machine to give tablets containing 50 mg. of active ingredient:

| | |
|---|---|
| 4-hydroxy-1,1-dimethyl-4-(9-xanthenyl)semicarbazide | 25% |

| | |
|---|---|
| Maize starch | 10% |
| Lactose | 20% |
| Magnesium stearate | 1% |
| Microcrystalline cellulose | to 100% by weight |

EXAMPLE 18

In the preparation of enteric coated tablets, tablets prepared as described in Example 17 were coated with sanderac varnish and then coated with cellulose acetate phthalate using a solution of 20% cellulose acetate phthalate and 3% diethyl phthalate in a mixture of equal parts of industrial alcohol and acetone.

EXAMPLE 19

In the preparation of tablets the following mixture was dry granulated and compressed in a tabletting machine to give tablets containing 5 mg. of active ingredient:- 4-hydroxy-1,1-dimethyl-4-(9-xanthenyl)-semicarbazide (10 g.), lactose (10 g.), and maize starch (5 g.).

EXAMPLE 20

In the preparation of enteric coated tablets, the tablets described in Example 19 were given a thin coat of shellac followed by 20 coats of cellulose acetate phthalate.

EXAMPLE 21

In the preparation of capsules, a mixture of the ingredients described in Example 19 was encapsulated in hard gelatin capsules. Enteric coating was applied by conventional dipping in cellulose acetate phthalate.

EXAMPLE 22

The following mixture was compressed into tablets in a conventional manner:

| | |
|---|---|
| 4-hydroxy-1,1-dimethyl-4-(9-xanthenyl)semicarbazide | 25% |
| Sodium bicarbonate | 75% |
| Peppermint oil | q.s. |

EXAMPLE 23

In the preparation of capsules a mixture of equal parts by weight of 4-hydroxy-1,1-dimethyl-4-(9-xanthenyl)semicarbazide and lactose was encapsulated in hard gelatin capsules, each capsule containing 50 mg. of the semicarbazide.

EXAMPLE 24

In the preparation of enteric coated capsules, the capsules of Example 23 were coated with cellulose acetate phthalate in the conventional manner.

EXAMPLE 25

Suppositories weighing 1g. and containing 50 mg. 4-hydroxy-1,1-dimethyl-4-(9-xanthenyl)semicarbazide were prepared in conventional manner using a base consisting of

| | |
|---|---|
| Polyethylene glycol 4000 | 33% |
| Polyethylene glycol 6000 | 47% |
| Water | 20% |

EXAMPLE 26

A solution for parenteral administration was prepared comprising 4-hydroxy-1,1-dimethyl-4-(9-xanthenyl)semicarbazide in propylene glycol, 100 mg./2 ml. sterilised by filtration.

Compositions similar to those described in Examples 16 – 26 were also prepared, containing other compounds of formula I previously described in place of 4-hydroxy-1,1-dimethyl-4-(9-xanthenyl)semicarbazide.

We claim:

1. Compounds of formula I

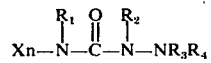

$$Xn-N-C-N-NR_3R_4 \quad \text{I}$$

with $R_1$, $O$, $R_2$ above the N, C, N respectively.

wherein Xn represents the group

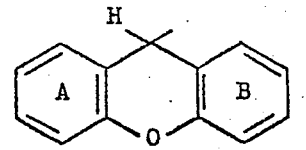

in which the rings A and B may optionally contain 1 additional substituent selected from halogen, lower-alkyl, lower-alkoxy and hydroxy, said substituent when present being in either the 1 or 2 position of the ring;
$R_1$ is hydrogen, lower-alkyl or lower-alkenyl;
$R_2$ is hydrogen or lower-alkyl;
$R_3$ is hydrogen or lower-alkyl;
$R_4$ is hydrogen or lower-alkyl;
together with pharmaceutically acceptable acid addition salts of compounds of formula I; and, when $R_3$ and $R_4$ are each lower-alkyl, pharmaceutically acceptable quaternary salts of compounds of formula I 2. Compounds of formula IA

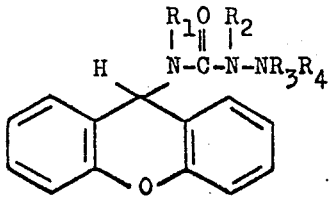

... IA in which
$R_1$ is hydrogen, lower alkyl or lower alkenyl;
$R_2$ is hydrogen or lower alkyl;
$R_3$ is hydrogen or lower alkyl;
$R_4$ is hydrogen or lower alkyl;
together with pharmaceutically acceptable acid addition salts of compounds of formula IA.

3. Compounds as claimed in claim 2 in which $R_1$ and $R_2$ are hydrogen, $R_3$ is hydrogen or lower alkyl and $R_4$ is hydrogen or lower alkyl.

4. The compound of claim 2 which is 4-(9-xanthenyl)semicarbazide.

5. The compound of claim 2 which is 1,1-dimethyl-4-(9-xanthenyl)semicarbazide.

* * * * *